United States Patent [19]

Preuss

[11] 4,446,072
[45] May 1, 1984

[54] PROCESS FOR DEGRADING THE 20-CARBOXYL GROUP OF Δ4-STEROID-20-CARBOXYLIC ACIDS

[75] Inventor: Wolfgang Preuss, Monheim, Fed. Rep. of Germany

[73] Assignee: Henkel KGaA, Duesseldorf, Fed. Rep. of Germany

[21] Appl. No.: 407,751

[22] Filed: Aug. 13, 1982

Related U.S. Application Data

[63] Continuation-in-part of Ser. No. 262,968, May 12, 1981, abandoned.

[30] Foreign Application Priority Data

May 12, 1980 [AT] Austria .................................. 2537/80
May 12, 1980 [AT] Austria .................................. 2538/80

[51] Int. Cl.$^3$ ................................................ C07J 5/00
[52] U.S. Cl. ............................ 260/397.45; 260/397.1; 260/397.4; 260/397.3
[58] Field of Search .............. 260/397.1, 397.45, 397.3

[56] References Cited

U.S. PATENT DOCUMENTS 4,072,710 2/1978 Coll .................................. 260/397.1

4,255,345 3/1981 Krbechek ......................... 260/397.1

OTHER PUBLICATIONS

Chemical Abstracts (1982), vol. 96 Par. 143171z.

Primary Examiner—Elbert L. Roberts
Attorney, Agent, or Firm—Ernest G. Szoke; Nelson Littell, Jr.

[57] ABSTRACT

Δ4-Steroid-20-carboxylic acids (BNC compounds) which may optionally contain at least one other double bond in the 1(2)- and/or 9(11)-position and which may also contain an oxygen function, particularly a hydroxyl group or a keto group, in the 11-position, are degraded in the 20-carboxyl group by carboxy inversion degradation. To achieve this, the BNC-carboxylic acids are first transformed into their acid halides which are reacted with peracids to form mixed acid anhydrides, followed by hydrolysis. The reaction product obtained is a mixture of 20-hydroxy- and 20(21)-ene-steroid compounds which contain one carbon atom less than the starting material used. New and known C21-steroid compounds can be produced by the process. The C21-steroid compounds having an oxygenated function in the 11-position may be processed to prednisolone and prednisone by known procedures.

11 Claims, No Drawings

PROCESS FOR DEGRADING THE 20-CARBOXYL GROUP OF Δ4-STEROID-20-CARBOXYLIC ACIDS

This is a continuation-in-part of Ser. No. 262,968, filed May 12, 1981 now abandoned.

BACKGROUND OF THE INVENTION

European Patent Application No. 004918 as laid open describes inter alia a process for the production of 17-C-steroid-α-propionic acid compounds by microbial side chain degradation on 17-C-side chain steroid substrates. In this way, it is possible in particular to produce 3-oxo-pregna-4-ene-20-carboxylic acid (Δ4-BNC) and/or 3-oxo-pregna-1,4-dien-20-carboxylic acid (Δ1,4-BNC). The process uses microorganism defect mutants which give steroid compounds containing the 17-C-α-propionic acid residue, even in the absence of inhibitors which inhibit degradation of the steroid ring and/or growth. These defect mutants are obtained and grown in accordance with the above-mentioned European Patent Application. A modification of this process is described in earlier European Patent Application No. 0015 308.

The structural formulae of Δ4-BNC and Δ1,4-BNC are as follows:

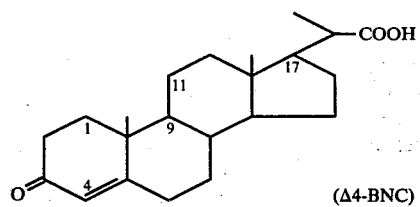

3-oxo-pregna-4-ene-20-carboxylic acid

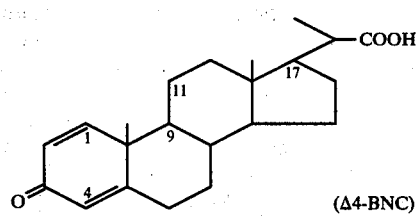

3-oxo-pregna-1,4-dien-20-carboxylic acid

German Offenlegungsschrift No. 28 39 033 describes structurally analogous steroid-20-carboxylic acids containing an additional double bond in the 9(11)-position and a process for their production. In particular, one possibility of producing Δ1,4,9(11)-BNC is described therein. U.S. Pat. No. 4,062,880 describes the structurally related Δ4,9(11)-BNC.

The hitherto mentioned BNC-compounds contain a functional group in only the 3-position of the ring system. However, all pharmacologically active corticosteroids contain additional oxygen functions. The 11,17 and 21 positions inter alia are particularly important in this respect. Normally, some of these oxygen functions are chemically introduced, including in particular the 17 and 21 positions.

By contrast, oxidation of the 11-position in steroid compounds is preferably carried out microbially. Several microbial steroid oxidations in the 11-position are described in the specialist literature. In this connection, reference is made to the following publications and to the original Articles quoted therein: F. Drawert "Biosynthese von Hydroxy-Verbindungen (Biosynthesis of Hydroxy Compounds);" Houben-Weyl "Methoden der organischen Chemie" (1978) 6/1d, pages 378–388; T. H. Stoudt, Adv. Appl. Microbial. 2 (1960), pages 190–195; and W. Charney and H. L. Herzog "Microbial Transformations of Steroids" Academic Press (1967), New York, page 29.

The microbial 11-hydroxylation of a variety of steroid compounds and the synthesis products obtained are described in these publications with numerous references to certain microorganism strains, particularly from the class of fungi.

The 11β-hydroxyl or 11-oxo configuration is generally required for strong pharmacological activity. Steroids hydroxylated in the 11β-position are obtained either by using microorganisms strains which introduce a hydroxyl group of the type in question stereoselectively or by using other microorganisms which hydroxylate in the 11α-position either predominantly or completely stereoselectively. In this case, the 11β-hydroxylated steroids are obtained by chemical oxidation to the 11-ketone in a first step, followed by reduction with a suitable reducing agent. The 11β-hydroxy compound can be formed stereoselectively. So far as the relevant literature on this subsequent chemical transformation is concerned, reference is made, for example, to: L. F. Fieser, M. Fieser "Steroide (Steroids)" Verlag Chemie (Weinheim 1961), 737 et seq., and to the original literature reference cited therein, J. Am. Chem. Soc. 77, 4436 (1955).

The production of Δ4- and/or Δ1,4-BNC compounds containing an oxygen function in the 11-position is described, for example, in German Offenlegungsschrift No. 28 39 033. In this process, the BNC-compounds unsubstituted in the 11-position are microbiologically oxidized in the 11-position under aerobic conditions in an aqueous nutrient medium. The production of 11α-hydroxy or 11β-hydroxy-1,4-BNC and 11-keto-1,4-BNC is described in particular.

Earlier European Patent Appln. No. 81 100 145.2 describes inter alia the hitherto unreported acid chloride of Δ1,4-BNC and a process for its production. Pregna-1,4-dien-3-one-20-carbonyl chloride (Δ1,4-BNC-chloride), other analogous acid halides of Δ1,4-BNC and corresponding acid halides of Δ4-BNC may be obtained by reacting the free acids with halogenating agents. The reaction is preferably carried out at at most moderately elevated temperatures, in particular, at temperatures not exceeding 15° C., and more especially, at temperatures below 5° C. It is also preferred to use the halogenating agent in a substantially stoichiometric quantity or in only a limited molar excess (up to about 10%). In addition, the reaction is best carried out in an inert solvent, for example, in halogenated hydrocarbons. It is possible in this way selectively to halogenate the 20-carboxyl group to form the corresponding acid chloride group without at the same time initiating any undesirable halogenation in the ring system of the steroid compound.

Analogous processes for the production of similar BNC-halides are the subject of my earlier copending, commonly assigned applications. Thus, U.S. patent application Ser. No. 262,971, filed May 12, 1981, abandoned in favor of its continuation-in-part Ser. No. 423,276, filed Sept. 24, 1982, describes the production of the halides of Δ4,9(11)-BNC which may even contain further double bonds, for example, in the 1(2)-position. U.S. patent application Ser. No. 262,965, filed May 12, 1981, abandoned in favor of its continuation-in-part Ser. No. 407,790, filed Aug. 13, 1982, describes the production of halides, particularly chlorides, of comparable BNC-compounds which, in the 11-position, contain an oxygen function and, in particular, a hydroxyl group or a keto group.

OBJECTS OF THE INVENTION

The object of the present invention is to provide a method by which it is possible, for example, starting out from Δ4-BNC and/or Δ1,4-BNC which may also contain an oxygen function in the 11-position, readily to obtain by chemical transformation of the side chain substituent in the 17-position intermediate products which may in turn be transformed without difficulty into pharmacologically desirable steroid compounds.

Another object of the invention is to apply a technique known per se for the degradation of carboxylic acids to compounds having a steroid structure of the type mentioned. Finally, the invention seeks to provide new C21-steroid compounds which are distinguished in particular by an oxygen function in the 11-position.

DESCRIPTION OF THE INVENTION

In a first embodiment, therefore, the present invention relates to a process for degrading the 20-carboxyl group of Δ4-steroid-20-carboxylic acids optionally containing at least one other double bond in the 1(2)- and/or 9(11)-position and corresponding to formula I:

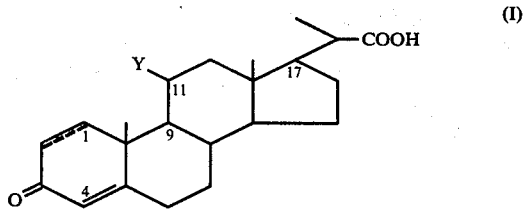

in which Y is hydrogen, a hydroxyl group or, together with the C-atom substituted by Y, represents a carbonyl group or may even be replaced by a 9(11)-ene bond, characterized in that the steroid-20-carboxylic acids are converted to their acid halides which are subjected to carboxy inversion degradation by reaction with peracids and hydrolysis of the reaction product and, if desired, the hydrolysis product is separated up into the 20-hydroxy and 20(21)-ene-steroid compounds formed.

According to the invention, this mixture of reaction products may be split up into its components, for example, by recrystallization or chromatographic separation.

The C20-alcohols may be converted into the corresponding progesterone derivatives by standard reactions of organic chemistry. In principle, the C20-(21)-alkenes may also be transformed by known methods into compounds which contain oxygen functions on C20–C21. Processes of this type are described, for example, in L. and M. Fieser, Steroide (Steroids), pages 677 et seq (Verlag Chemie, Weinheim/Bergstrasse, 1961) and in the original literature cited therein. The C20-alkenes are transformed into derivatives of the cortexone type.

The degradation of carboxylic acids to alcohols by the carboxy inversion reaction using peracids and hydrolysis of the reaction product is described in the literature, cf. J. Org. Chem. 30, 3760 (1965), D. B. Denney, N. Sherman "Degradation of Acids to Alcohols by the Carboxy-Inversion Reaction." In this first publication of this process, however, the reaction is only described with reference to simple aliphatic carboxylic acids. The application of this reaction to compounds having a partial steroid structure is described in J. Org. Chem. 38, 3040 (1973), cf. in particular, pages 3041/3042. However, this degradation has not been used for the production of intermediate products for the synthesis of steroid hormones (particularly adrenal cortical hormones) which, in addition, contain partial structures of the A-ring type in Δ4-BNC and Δ1,4-BNC and, optionally, other reactive sites in the ring skeleton. The fact that it can be applied without difficulty under the process conditions described in detail in the following and the results obtained could not be predicted with any certainty by the expert.

The process according to the invention is carried out under the following conditions.

The particular BNC-starting compound is first transformed into the corresponding 20-acid halide, particularly the acid chloride. This first step is carried out in accordance with my copending applications mentioned above. Thus, it is possible, for example, to prepare the acid chloride from the free steroid carboxylic acid, with advantage at temperatures in the range from 0° to 5° C., in methylene chloride and using a slight excess of thionyl chloride as the chlorinating agent. A catalytic quantity of pyridine accelerates the reaction, particularly in the case of Δ4-BNC, but is not absolutely essential.

Instead of using methylene chloride, it is possible to use other inert solvents, for example, chloroform or ethers. It is also possible to use other chlorinating agents, for example, phosphorus trichloride or phosphorus pentachloride, although thionyl chloride is preferred. The pyridine used as catalyst may also be replaced by dimethyl formamide.

Instead of using the above-mentioned chlorinating agents, it is possible to use other halogenating agents, for example, thionyl bromide, phosphorus tribromide or phosphorus pentabromide which give the corresponding acid bromide.

The 20-carboxyl group is then degraded by the carboxy inversion reaction in which the acid halide is reacted with a peracid, followed by hydrolysis of the rearrangement product formed from the mixed peracid anhydride, see the already mentioned Article in J. Org. Chem. 30, 3760 (1965) D. B. Denney, N. Sherman "Degradation of Acids to Alcohols by the Carboxy-Inversion Reaction."

According to the invention, m-chloroperbenzoic acid is preferably used as the peracid for forming the mixed peracid anhydride. This compound is available in commercial quantities, is relatively safe to handle and ensures a smooth reaction. Instead of using m-chloroperbenzoic acid, however, it is also possible to use other peracids, perferably aromatic peracids, particularly those having an electron-attracting residue on the aromatic nucleus, such as p-nitroperbenzoic acid.

The reaction of the steroid-20-carboxylic acid chloride with the peracid, particularly m-chloroperbenzoic acid, is carried out at temperatures in the range of from −50° C. to room temperature. The preferred reaction temperatures are in the range from −10° C. to −30° C. The reactants are used in substantially stoichiometric quantities. It may be advisable to use the peracid in a slight excess.

The reaction is best carried out in an inert solvent in the presence of a base. Suitable solvents are, for example, halogenated hydrocarbons, such as methylene chloride or chloroform, ethers, such as diethyl ether or tetrahydrofuran, nitriles, such as acetonitrile, acid amides, such as dimethyl formamide, or ketones, such as acetone, for example. The preferred inert diluents are solvents having a certain polarity. Particularly suitable bases are tertiary nitrogen bases, such as, for example, pyridine, methyl pyridines, N,N-dimethylamino pyridine, triethyl amine or ethyl diisopropyl amine. Both cyclic and also open-chain tertiary amines may be used. However, it is also possible to use inorganic basic components, particularly basic salts of strong bases and weak, particularly volatile acids. One suitable example is lithium carbonate. The base is preferably used at least in quantities sufficient to bind the hydrogen halide formed during the reaction.

The reaction is preferably carried out by initially adding the peracid to the solution of the steroid carboxylic acid halide in the inert solvent after cooling to the required starting temperature of the reaction, for example, after cooling to −30° C., and then carefully introducing the basic component in portions with stirring and cooling. The reaction mixture is then left for a prolonged period, for example, overnight, to heat to room temperature, after which most of the solvent is distilled off.

In the following stage of the reaction, the reaction product initially formed is subjected to hydrolysis. Hydrolysis is preferably carried out under basic conditions, best under basic/alcoholic conditions. Alcoholic potassium or sodium hydroxide, for example, is suitable for hydrolysis. The hydrolysis step is preferably carried out at moderate temperatures, for example, of the order of 0° C. The basic component is preferably used in an excess amount to several times the quantities of acid used. For example, the amount of base used for hydrolysis may amount to between three and eight times the stoichiometric quantity, based on the steroid carboxylic acid used. Four to six fold quantities of base are preferred here.

On completion of the reaction, the hydrolysis product is concentrated and then taken up in an inert, water-immiscible solvent, for example, methylene chloride, washed and then concentrated to dryness.

The crude product thus obtained is a mixture of the 20-hydroxy and 20-ene compounds. The hydroxy compound is normally present in larger quantities than the 20(21)-olefin. The components of this crude reaction mixture may be separated from one another, for example, by chromatographic processes.

It has surprisingly been found that, in the process according to the invention, the newly created olefinic bond always appears in the 20(21)-position, but never, not even partly, in the 17(20)-position.

Where the carboxy-inversion reaction using peracids is applied to the BNC-compounds employed in accordance with the invention, some known and some new compounds are formed as reaction products, depending upon the starting compound used. The new steroid derivatives obtainable in accordance with the invention fall within the scope of the invention.

In an additional embodiment, therefore, the present invention relates to new Δ20(21)-C21-steroid compounds having an oxygen function in the 11-position and corresponding to formula II:

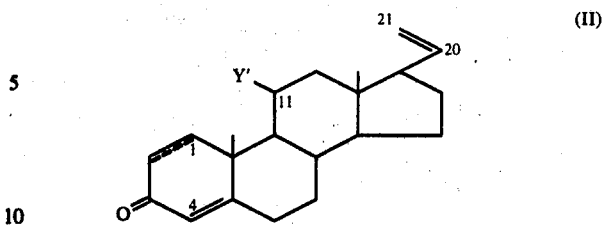

in which Y' is a hydroxyl group or, together with the C-atom substituted by Y', represents a carbonyl group.

Δ4- and Δ1,4-compounds of this type which contain an additional olefinic double bond in the 20(21)-position and, in addition, one of the above-mentioned oxygen functions in the 11-position are hitherto unknown compounds. Accordingly, the invention relates more particularly to pregna-1,4,20-trien-3,11-dione and pregna-4,20-dien-3,11-dione as new compounds. The corresponding derivatives containing an 11-hydroxy group, namely, 11-hydroxy-pregna-1,4,20-trien-3-one and 11-hydroxy-pregna-4,20-dien-3-one also fall within the scope of the invention. These hydroxy compounds may contain the 11-hydroxy group in α- or in β-form. The β-form can be of advantage for pharmacological purposes, although as mentioned the α-form may be transformed into the β-form. The 11-hydroxy compounds may also be transformed into corresponding 11-keto compounds by oxidation.

The new steroid alkenes corresponding to formula II are thus of particular interest as an intermediate stage in the synthesis of steroid hormones having an oxygen function on the 11 carbon.

In the case of the reaction products containing a hydroxyl group in the 20-position, the carboxy inversion degradation proposed in accordance with the invention gives compounds which for the most part are known. However, this subclass of the products obtained in accordance with the invention also includes hitherto undescribed representatives which fall within the scope of the invention. Of these, 20-hydroxy-pregna-1,4-dien-3,11-dione, i.e., a steroid compound containing a carbonyl group in the 11-position, is particularly significant. The hydroxy group in the 20-position may exist both in the α-configuration and also the β-configuration. According to the invention, the 20-α-compounds may be obtained as direct products of the process. Another new compound according to the invention is 11-hydroxy-20-α-hydroxy-pregna-1,4-dien-3-one in which the hydroxy group in the 11-position may be both in the α-form and also in the β-form. The foregoing observations on compounds of this type apply here.

Steroid derivatives of the progesterone type may be prepared from the new C20-alcohols having the indicated structures and also from the C20-alcohols known per se obtainable in accordance with the invention by reactions of the type commonly applied in organic chemistry.

By oxidation of the new C20-alcohols having the formula III:

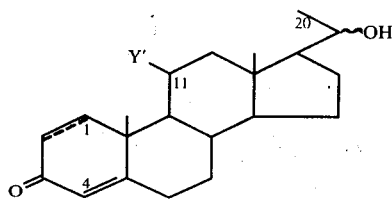

(III)

wherein Y' is selected from the group consisting of hydroxyl, and, together with the C-atom substituted by Y', a carbonyl, with pyridinium chlorochromate according to the process of Corey et al, Tetrahedron Letters, 2647-2650 (1975), the-known-from-the-literature corresponding 20-keto compound is obtained in yields of about 80%. Thus either 20-hydroxy-pregna-1,4-dien-3,11-dione or 11-hydroxy-20α-hydroxy-pregna-1,4-dien-3-one are oxidized by pyridinium chlorochromate to give the known progesterone derivative pregna-1,4-dien-3,11-20-trione. This trione is described in U.S. Pat. No. 2,128,238.

Pregna-1,4-dien-3,11,20-trione can be converted to the method of Hogg et al, J. Am. Chem. Soc. 77, 4438 (1955) into the known methyl 3,11-dioxo-pregna-1,4,17-trien-21-oate. The further transformation of the 17(20) unsaturated esters, via the respective 21-hydroxy-pregnane derivatives into corticoids such as prednisone and prednisolone has likewise been described by Hogg et al, J. Am. Chem. Soc. 77, 4438 (1955). An improved reduction step for the preparation of the 21-hydroxy-compound is described in my commonly assigned U.S. patent application Ser. No. 262,969, filed May 12, 1981, now U.S. Pat. No. 4,370,271.

The following examples are illustrative of the invention without being limitative.

EXAMPLE 1

Degradation of Δ1,4-BNC to 20-hydroxy-pregna-1,4-dien-3-one (A) and pregna-1,4,20(21)-trien-3-one (B)

Δ1,4-BNC is first transformed into the corresponding acid chloride:

4.0 ml (55 mMols) of thionyl chloride freshly distilled over squalene are added at 0° C. to 17 gm (50 mMols) of Δ1,4-BNC in 100 ml of absolute $CH_2Cl_2$, followed by stirring for 20 minutes at 0° C. The solvent and excess thionyl chloride are then removed in vacuo at the same temperature. The residue is again taken up in methylene chloride and the solution re-concentrated to dryness. The residue may be used for further reactions.

In order to obtain an acid chloride suitable for analysis, the crude acid chloride is digested with absolute ether and dried after the ether has been carefully distilled off in an oil pump vacuum.

The acid chloride is dissolved in 100 ml of absolute $CH_2Cl_2$, after which a solution of 10.0 gm of m-chloroperbenzoic acid (90%, remainder m-chlorobenzoic acid) in 100 ml of absolute methylene chloride and then a solution of 60 mMols of dry pyridine in a little absolute $CH_2Cl_2$ are added dropwise at −40° C. and the mixture is left standing overnight to come to room temperature.

Most of the solvent is removed in vacuo. 125 ml of 2 N methanolic potassium hydroxide are added to the residue and the mixture stirred for several hours at room temperature. Some of the methanol is distilled off in vacuo, taken up in methylene chloride and the methylene chloride phase successively washed with water, dilute sulfuric acid and again with water.

Drying of the organic phase and removal of the solvent leaves 14.6 gm of a crystalline residue containing 60% of (A) and 30% of (B). (A) and (B) may be separated from one another by chromatography on a column of silica gel.

Melting point of the 20-α-hydroxy-pregna-1,4-dien-3-one (A): 161° C. to 166° C.;

Melting point of the pregna-1,4,20(21)-trien-3-one (B): 170° C. to 171° C./lit; 166° to 167° C. in J. C. S. Perkin I, 2064 (1979).

MS, IR and NMR-spectra confirm the structures of the reaction products as indicated here.

It is surprising that, apart from the alcohol (A), only the alkene (B) with the 20(21)-double bond is selectively formed during degradation of the acid chloride. The alkene containing the 17(20)-double bond, which is also possible in principle, could not be found.

EXAMPLE 2

20α-hydroxy-pregna-1,4-dien-3,11-dione and pregna-1,4,20-trien-3,11-dione (a) Pregna-1,4-dien-3,11-dione-20-carbonyl chloride.

0.12 ml (1.6 mMols) of thionyl chloride freshly distilled over squalene and a small drop of pyridine are added at 0° C. to 500 mg (1.4 mMols) of Δ1,4,11-oxo-BNC in 8 ml of dry $CH_2Cl_2$. After one hour, the solvent and excess thionyl chloride were removed in vacuo at 0° C. 5 ml of absolute methylene chloride are added to the residue, followed by reconcentration to dryness. The crude acid chloride is formed in a yield of 495 mg.

(b) 300 mg of dried 85% m-chloroperbenzoic acid in 5 ml of methylene chloride and then 0.14 ml of pyridine in 2 ml of $CH_2Cl_2$ are added dropwise at −30° C. to a solution of the acid chloride in 5 ml of absolute methylene chloride. The mixture is left standing overnight to heat to room temperature, after which (most of) the solvent is distilled off and methanolic potassium hydroxide (7 mMols KOH) is added to the residue at 0° C. After about six hours at room temperature, the product is concentrated, taken up in methylene chloride and the methylene chloride phase successively washed twice with water, with dilute sulfuric acid and again with water, dried over $Na_2SO_4$ and then concentrated to dryness. Gross yield: 365 mg.

Separation by column chromatography (silica gel, methylene chloride/ethyl acetate 90:10 to 70:30) produced 230 mg (50%) of the 20α-hydroxy compound and 100 mg (23%) of the alkene in thin-layer-chromatographic purity. For determining melting point and for elemental analysis, samples were finely purified by preparative high pressure liquid chromatography and re-crystallized from isopropanol.

20αOH:

Melting point: 237°-239° C. (decomp.).

$C_{21}H_{28}O_3$: Obs. C 76.34%, H 8.43%. Calc. C 76.79%, H 8.59%.

20(21)-ene:

Melting point: 115°-126° C.

$C_{21}H_{26}O_2$: Obs. C 81.02%, H 8.16%. Calc. C 81.25%, H 8.44%.

Both structures were confirmed by MS, IR and $^1H$-NMR.

EXAMPLE 3

11β,20α-dihydroxy-pregna-1,4-dien-3-one and 11β-hydroxy-pregna-1,4,20-trien-3-one (a) 11β-hydroxy-pregna-1,4-dien-3-one-20-carbonyl chloride.

Preparation was carried out in the same way as in Example 2(a). To verify the yield, the crude reaction product was converted into the methyl ester. Yield: 88%.

(b) The carboxy-inversion degradation was carried out in accordance with Example 2(b). 218 mg (47%) of 20α-OH compound and 122 mg (28%) of 20(21)-alkene were isolated in pure form [fine purification as in Example 2(b)] from 500 mg of the 11β-hydroxy acid.

20α-OH:
Melting point: 210°–216° C.
$C_{21}H_{30}O_3$: Obs. C 76.59%, H 9.31%. Calc. C 76.32%, H 9.15%.

20(21)-ene:
Melting point: 217°–222° C.
$C_{21}H_{28}O_2$: Obs. C 80.61%, H 9.25%. Calc. C 80.73%, H 9.03%.

The structures were confirmed by MS, IR and $^1$H-NMR.

EXAMPLE 4

Degradation of Δ4-BNC to 20-hydroxypregna-4-en-3-one and pregna-4,20(21)-dien-3-one Three drops of pyridine and 1.03 ml (14.2 mMols) of thionyl chloride, freshly distilled over squalene, were added at 0° C. to 8.5 gm (25 mMols) of Δ4-BNC in 100 ml of dry $CH_2Cl_2$. After stirring for one hour at 0° C., the same quantity of $SOCl_2$ was again added. After another hour, $CH_2Cl_2$ and excess thionyl chloride were removed in vacuo. The residue was taken up in a little $CH_2Cl_2$ and reconcentrated to dryness.

Further reaction and working up were carried out in the same way as described in Example 1 for the degradation of Δ1,4-BNC. 6.1 gm of a crystalline residue were obtained.

Chromatography on silica gel produced 3.3 gm of 20-hydroxy-pregna-4-en-3-one (melting point 163°–166° C.) and 1.8 gm of pregna-4,20(21)-dien-3-one (melting point 122°–124° C.). The structures were confirmed by MS-, IR- and NMR-spectra.

I claim:

1. A process for degrading the 20-carboxylic acid halide group of Δ4-steroid-20-carboxylic acid halides optionally containing at least one other double bond in the 1(2)- and/or 9(11)-position corresponding to formula I:

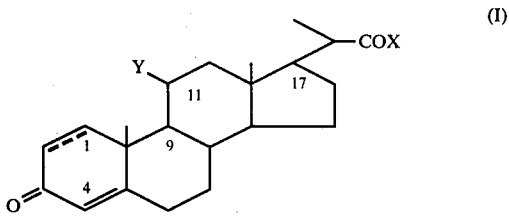

in which Y is a member selected from the group consisting of hydrogen, hydroxyl and, together with the C-atom substituted by Y, carbonyl, and a 9(11)-ene bond, and X represents a halide, characterized in that said Δ4-steroid-20-carboxylic acid halides are subjected to carboxy inversion degradation by reaction with an aromatic percarboxylic acid and hydrolysis of the reaction product under basic/alcoholic conditions and said 20-hydroxy and 20(21)-ene steroid compounds formed are recovered.

2. The process of claim 1 wherein said aromatic percarboxylic acid has an electron-attracting residue on the aromatic nucleus.

3. The process of claim 2 wherein said percarboxylic acid is m-chloroperbenzoic acid.

4. The process of claim 1 or 2 or 3 wherein said reaction of carboxy inversion degradation is carried out at temperatures of from −50° C. to room temperature.

5. The process of claim 4 wherein said reaction of carboxy inversion degradation is carried out in an inert solvent.

6. The process of claim 4 wherein said reaction of carboxy inversion degradation is carried out in the presence of a basic compound.

7. The process of claim 6 wherein said basic compound is a tertiary amine.

8. The process of claim 5 wherein said reaction of carboxy inversion degradation is carried out in the presence of a basic compound.

9. The process of claim 8 wherein said basic compound is a tertiary amine.

10. 20-Hydroxy-pregna-1,4-dien-3,11-dione.

11. 11-Hydroxy-20α-hydroxy-pregna-1,4-dien-3-one.

* * * * *